United States Patent [19]

Lübbers

[11] Patent Number: 4,606,351

[45] Date of Patent: Aug. 19, 1986

[54] OPTICAL INDICATOR DEVICE FOR THE REMOTE MEASUREMENT OF PHYSICAL CHANGES IN A TEST SUBJECT

[75] Inventor: Dietrich W. Lübbers, Dortmund, Fed. Rep. of Germany

[73] Assignee: Max Planck Gesellschaft zur Foerderung der Wissenschaften, Goettingen, Fed. Rep. of Germany

[21] Appl. No.: 142,141

[22] Filed: Apr. 14, 1980

[30] Foreign Application Priority Data

Apr. 14, 1979 [DE]  Fed. Rep. of Germany ....... 2915367

[51] Int. Cl.$^4$ .............................................. A61B 5/00
[52] U.S. Cl. ..................................... 128/633; 128/665; 128/736; 250/458.1; 374/162; 435/14
[58] Field of Search ............... 128/633, 636, 665, 736; 23/901, 203 LC; 250/458, 459, 461 R, 461 B, 458.1; 435/14; 422/79; 73/356; 374/162

[56] References Cited

U.S. PATENT DOCUMENTS

| | | | |
|---|---|---|---|
| 3,313,290 | 4/1967 | Chance et al. ...................... | 128/633 |
| 3,791,988 | 2/1974 | Josef et al. ......................... | 23/901 X |
| 3,872,050 | 3/1975 | Benton et al. ..................... | 350/351 X |
| 3,960,753 | 6/1976 | Larrabee .......................... | 23/230 LC |
| 3,993,809 | 11/1976 | Schranz et al. ................... | 73/355 R X |
| 4,003,707 | 1/1977 | Lubbers et al. ................... | 128/633 X |
| 4,016,761 | 4/1977 | Rozzelle ............................ | 73/356 |
| 4,018,651 | 4/1977 | Canto et al. ...................... | 435/14 |
| 4,071,020 | 1/1978 | Pugliese ........................... | 250/461 B X |
| 4,215,275 | 7/1980 | Wickersheim ................... | 128/736 X |
| 4,215,940 | 8/1980 | Lubbers et al. .................. | 356/41 X |
| 4,245,507 | 1/1981 | Samulski .......................... | 73/356 |
| 4,255,053 | 3/1981 | Lubbers et al. .................. | 356/417 X |
| 4,269,516 | 5/1981 | Lubbers et al. .................. | 356/427 |
| 4,272,484 | 6/1981 | Lubbers ............................ | 422/68 |
| 4,306,877 | 12/1981 | Lubbers .......................... | 128/633 X |

*Primary Examiner*—Kyle L. Howell
*Assistant Examiner*—John C. Hanley
*Attorney, Agent, or Firm*—Michael J. Striker

[57] ABSTRACT

An optical indicator device for the remote indication and measurement of physical changes in a living body includes at least one source of light disposed remote from the test subject and at least one indicator disposed in direct contact with the test subject. This indicator includes a fluid-tight, light-permeable membrane which encloses an inner space. A liquid crystal compound is disposed in the inner space. This compound is of the opto-electrical type adapted to respond to light waves from said source of light and furthermore responsive to physical changes in the space surrounding said indicator. Detector means are provided for indicating and measuring the response of said liquid crystal compound to said light rays and physical changes. Preferably, the indicator device is combined with a similar device containing a different liquid crystal for measuring the glucose concentration. Thus, the device permits to measure the temperature in the test area of the test subject and simultaneously to measure the glucose concentrations prevailing therein.

2 Claims, 1 Drawing Figure

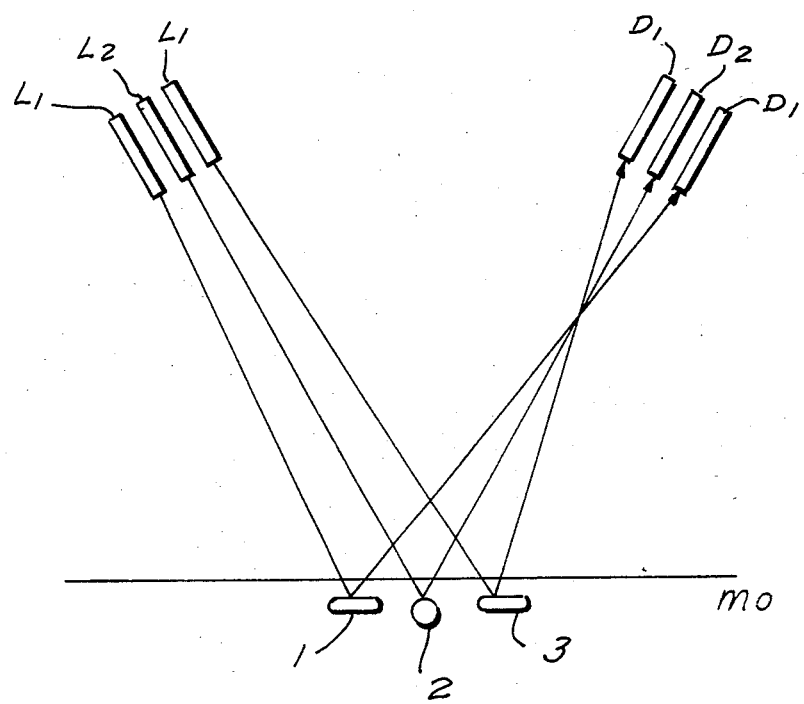

OPTICAL INDICATOR DEVICE FOR THE REMOTE MEASUREMENT OF PHYSICAL CHANGES IN A TEST SUBJECT

BACKGROUND OF THE INVENTION

This invention relates to an optical indicator device.

Optical indicator devices have already been used biologically for the measurement of concentrations of specific particles. In these devices the indicator was provided with a membrane which was permeable in a selective manner by specific particles through diffusion and means were provided at the opposite side of the membrane to cause the optical indication of the concentration of particles which had penetrated the membrane. Through the separation of the specific particles entering the inner indicator space from the known amount of other particles, a fairly exact measurement could be accomplished.

This type of measurement and indicating device is free of undesirable reaction on the test subject and furthermore is not likely to result in wrong measurements. The device, besides, is quite sturdy and can be used without special preparation. This type of indicator has, however, heretofore been used only for measuring concentrations. Indicators for measuring other physical parameters have not been available. However, in biological practice which has to do with living tissue the measurement of pressure or temperature is extremely important if a reaction on the test subject through undesirable degrees of concentration is to be excluded.

For instance, the control of the temperature parallel with the measurement of the glucose concentration is of great significance since there occur temperature variations up to 10% which, for instance in case of diabetics, are not tolerable.

It is therefore an object of the present invention to provide for indicators which are optically responsible to physical parameters. An incidental object is that such indicators must be available without undue expense and must be usable without complex preparations.

ESSENCE OF THE INVENTION

This object in its essence is solved by using indicators in which the indication is effected by a substance forming a mesophase. Such materials are generally known as liquid crystals. They have been used as optoelectrical indicators. However, their use for biological purposes in living test subjects is believed novel.

If the indicator for instance is in the form of a microcapsule these materials can be embedded in living tissue so as to provide for a remote control of the temperature of a specific tissue layer. In general technology methods are known to measure the color- or fluorescence variations occurring through transparent surfaces which may have been contaminated with interfering materials. For the measurement of the temperature a liquid crystal forming a cholesteric phase is particularly suited.

It is preferred to use indicator spaces for measuring the glucose concentration simultaneously with an indicator as above described and containing a cholesteric compound for determining the temperature. This makes it possible to control both the glucose concentration and the temperature which will often avoid critical conditions in diabetics in intensive care patients.

The usefulness of the indicators of the invention can be made available for other purposes by employing liquid crystals in a nematic phase. These indicators will permit also to measure mechanical pressure, mechanical impulses and electrical or magnetic fields.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

The drawing in diagrammatical form indicates a device according to the present invention.

DETAILS OF THE PREFERRED EMBODIMENT

With reference to the drawing it will be seen that a test subject MO is provided with an indicator capsule 1 which may be embedded in its tissue. This capsule comprises an oxygen permeable membrane and the space within the membrane is filled with a pyrene buteric acid compound.

In addition there is provided a measuring capsule 2 which has an optically permeable, fluid-tight membrane and in which is disposed in its inner space a compound consisting of dipalmitoyl phosphatidylcholine+1-aniline-8-naphthalene sulfonate. An additional indicator capsule 3 contains pyrene buteric acid and glucoseoxydase.

$L_1$ indicates monochromators for generating light to cause fluoresence of the pyrene buteric acid. $L_2$ indicates a source of light for causing fluoresence of the 1-aniline-8-naphthalene sulfonate.

The light detectors are indicated by the reference letter $D_1$ for the detector for the fluorescent light of the pyrene buteric acid and as $D_2$ for the detector for the fluorescent light of the naphthalene sulfonate.

Any glucose present in the test subject can be measured as follows.

In the indicator capsule 1 having a glucose-permeable membrane the amount of oxygen present in the subject is measured. In the oxygen capsule 3 having a glucose-permeable membrane a measurement is effected of the proportion of oxygen which remains after the glucose which entered the indicator capsule 3 has reacted with oxygen due to the presence of the glucoseoxydase in that capsule. There can thus be determined the oxygen difference, i.e. oxygen residue between the measurement in capsule 1 and the measurement in capsule 3. This difference is proportional to the glucose concentration which can thus be determined with corresponding detectors.

Simultaneously the temperature in the reaction space of the indicator capsule 2 is continuously controlled since any change of the temperature will result in a variation of the intensity of the fluoresent light emanating from the indicator capsule 2.

Without further analysis, the foregoing will so fully reveal the gist of the present invention that others can, by applying current knowledge, readily adapt it for various applications without omitting features that, from the standpoint of prior art, fairly constitute essential characterisetics of the generic or specific aspects of this invention.

What is claimed as new and desired to be protected by Letters Patent is set forth in the appended claims:

1. An optical indicator device for the remote indication and measurement of physical changes in a test subject, the said device comprising at least one source of light which is a monochromator remote from the test subject, the said indicator including a fluid-tight, light-permeable membrane enclosing an inner space,
   a liquid crystal compound disposed in said inner space of the indicator, the said compound being adapted to be excited by light vaves from said source of light, so as to become fluorescent, and wherein said liquid crystal compound is further adapted to undergo variations in the intensity of such fluorescence in response to variations in temperature,
   detector means for indicating and measuring the variations in the intensity of the fluorescence in and the response of said compound to said light waves, and two additional indicators, disposed in direct contact with said test subject, a first additional indicator having an oxygen permeable membrane enclosing said inner space and having a prene butyric acid compound in said inner space, the said compound being adapted to become fluorescent in response to the light waves from one of said sources of light and being adapted to undergo changes in the intensity of such fluorescence in response to amount of oxygen, and a second of said additional indicators likewise being provided with an oxygen permeable and glucose permeable membrane and having in its inner space pyrene butyric acid together with glycose oxidase, the glycose oxidase being adapted to react with permeating gluose, a difference of measurement of the pure oxygen in the first additional indicator and of the oxygen residue, after reaction of the glucose with the glycose oxidase, in the second additional indicator resulting in a difference of the intensity of the fluorescence in said two additional indicators which difference is proportional to glucose concentration, thus enabling corresponding detectors to measure glucose concentration in said test subject while said detector means determines simultaneously temperature prevailing surrounding said first defined indicator.

2. The indicator device of claim 1, wherein the indicator for measuring the temperature contains a liquid crystal of the cholesteric type.

* * * * *